United States Patent
Dobric et al.

(10) Patent No.: US 9,345,754 B2
(45) Date of Patent: *May 24, 2016

(54) ALLOGENEIC TUMOR THERAPEUTIC AGENT, A VACCINE USING ALLOGENEIC TUMOR CELLS FOR THE THERAPEUTIC TREATMENT OF TUMOR DISEASES, AND A METHOD FOR THE MAKING OF SUCH A VACCINE, AND TRANSFECTED HUMAN TUMOR CELLS FOR USE AS A VACCINE

(75) Inventors: Tomislav Dobric, Berlin (DE); Burghardt Wittig, Berlin (DE); Manuel Schmidt, Berlin (DE)

(73) Assignee: Mologen AG, Berlin (DE)

( * ) Notice: Subject to any disclaimer, the term of this patent is extended or adjusted under 35 U.S.C. 154(b) by 199 days.

This patent is subject to a terminal disclaimer.

(21) Appl. No.: 12/614,985

(22) Filed: Nov. 9, 2009

(65) Prior Publication Data

US 2010/0297189 A1  Nov. 25, 2010

Related U.S. Application Data

(60) Division of application No. 11/482,233, filed on Jun. 30, 2006, now Pat. No. 7,635,468, which is a continuation-in-part of application No. PCT/DE2004/000859, filed on Apr. 20, 2004.

(30) Foreign Application Priority Data

Dec. 30, 2003  (WO) ...................... PCT/DE03/04299

(51) Int. Cl.
*A61K 39/00* (2006.01)
*C12N 5/09* (2010.01)

(52) U.S. Cl.
CPC .......... *A61K 39/0011* (2013.01); *C12N 5/0693* (2013.01); *A61K 2039/5152* (2013.01); *A61K 2039/5156* (2013.01); *A61K 2039/55516* (2013.01); *A61K 2039/55522* (2013.01); *A61K 2039/55527* (2013.01); *A61K 2039/55561* (2013.01); *C12N 2510/00* (2013.01)

(58) Field of Classification Search
CPC ............. C12N 5/0693; C12N 2510/00; A61K 2039/5152; A61K 2039/55522; A61K 2039/55561

See application file for complete search history.

(56) References Cited

U.S. PATENT DOCUMENTS 5,681,562 A  10/1997 Sobol et al.
6,039,941 A  3/2000 Blankenstein et al.

FOREIGN PATENT DOCUMENTS

| CM | 1186121 A | 7/1998 |
|---|---|---|
| DE | WO 93/06867 | 4/1993 |
| DE | WO 00/04918 | 2/2000 |
| DE | WO 01/07055 | 2/2001 |
| DE | WO 02/060476 | 8/2002 |
| DE | WO 03/031469 | 4/2003 |
| DE | WO 03/045428 | 6/2003 |
| DE | WO 2004/016788 | 2/2004 |
| EP | 0686-697 | 5/1995 |
| WO | WO 02060476 A2 | 8/2002 |
| WO | 02100345 A2 | 12/2002 |
| WO | WO 03045428 A2 | 6/2003 |
| WO | 2006063301 | 6/2006 |

OTHER PUBLICATIONS

Kaufmann et al. Immunobiol 2000;202:339-52.*
Ling et al. Oncogene Mar. 2006;25:4483-90.*
Wang et al. J Immunol 2005;174:6113-21.*
Sin et al. Clin Diagnostic Lab Immunol 2000;7:751-8.*
Finke et al., 1997; Cancer Gene Ther. 4: 260-268.
Wittig et al., 2001, Human Gene Therapy 12:267-278.
Sun Y. et al., 2000, Gene Therapy (17): 1467-76.
Palllard, 1998, Hum. Gene Thar. 9: 2457-2458.
Schadendorf et al. 1995, J. Mol. Med. 73: 473-477.
Jäger et al., 1996, Int J Cancer. 67(1):54-62.
Miller et al., 1993 Blood 18: 3686-3694.
Murphy et al., 1993, J. Clin. Invest. 92: 1918-1924.
Jicha et al., 1991, J. Exp. Med. 174: 1511-1515.
Hock et al. 1993, Cancer Res. 53. 714-716.
Cayeux S. et al., 1995, Eur J Immunol. Aug. 25, 1995: (8)2325-31.
Schmidt-Wolf et al., 1989, J. Immunol, Methods 125: 185-189.
Sato et al., 1996, Science 273: 352-354.
Liu HM et al., Blood 1998; 92(10):3730-6.
Foa et al., 1994, Nat. Immun. 13: 65-75.
Schakowski et al., 2001, Molecular Therapy vol. 3.
Köchling Joachim et al., 2003, Clinical Cancer Research vol. 9.
Vereecque R et al., 2000, Gene Theray 7.
Noguchi M et al., 2001, Cancer Gene Therapy, vol. 8.
Chiodoni C et al., 1999, Rockefeller U. Press vol. 190.
Guo et al., "TK gene combined with mIL-2 and mGM-CSF genes in treatment of gastric cancer," World J Gastroenterol 2003;9(2):233-237.
Cayeux, et al., "Influence of gene-modified (IL-7, IL-4, and B7) tumor cell vaccines on tumor antigen presentation," Journal of Immunology, Mar. 1997, vol. 158, No. 6, pp. 2834-2841.

* cited by examiner

*Primary Examiner* — Janice Li
(74) *Attorney, Agent, or Firm* — 24IP Law Group; Timothy R DeWitt (57) ABSTRACT

A vaccine on the basis of allogeneic tumor cells for the therapeutic treatment of defined tumor diseases, and a method for the making of such vaccine is disclosed. The tumor cells were previously transfected ex vivo with expression constructs encoding cytokines and co-stimulatory factors.

20 Claims, 3 Drawing Sheets

SEQUENCE LISTING

```
<160> NUMBER OF SEQ ID NOS: 1

<210> SEQ ID NO 1
<211> LENGTH: 116
<212> TYPE: DNA
<213> ORGANISM: Artificial
<220> FEATURE:
<223> OTHER INFORMATION: Immune Stimulatory Sequence
<220> FEATURE:
<221> NAME/KEY: misc_feature
<223> OTHER INFORMATION: Synthetic Oligo
```

```
<400> SEQUENCE: 1
cctagggatt accaccttca ttggaaaacg ttcttcgggg cgttcttagg tggtaacccc    60
taggggttac caccttcatt ggaaaacgtt cttcggggcg ttcttaggtg gtaacc       116
```

ALLOGENEIC TUMOR THERAPEUTIC AGENT, A VACCINE USING ALLOGENEIC TUMOR CELLS FOR THE THERAPEUTIC TREATMENT OF TUMOR DISEASES, AND A METHOD FOR THE MAKING OF SUCH A VACCINE, AND TRANSFECTED HUMAN TUMOR CELLS FOR USE AS A VACCINE

CONTINUING APPLICATION DATA

This application is a Continuation-In-Part application of International Patent Application No. PCT/DE2004/000859, filed on Apr. 20, 2004, which claims priority from International Patent Application No. PCT/DE2003/04299, filed on Dec. 30, 2003. International Patent Application No. PCT/DE2004/000859 was pending as of the filing date of this application. The United States was an elected state in International Patent Application No. PCT/DE2004/000859.

BACKGROUND

1. Technical Field

The application concerns a vaccine on the basis of allogeneic tumor cells for the therapeutic treatment of tumor diseases, as well as a method to make such vaccine. Furthermore, the application concerns transfected human tumor cells for use as a vaccine.

2. Background Information

Apart from conventional methods to treat cancerous diseases, such as radiation and chemotherapy, which since the 1950's comprise the only option to treat advanced and disseminated tumor diseases, immunotherapy seems to be a promising approach when confronted with metastasizing tumors.

Immunotherapy aims to enhance the natural response against the tumor disease by means of modifications derived from the repertoire of gene technology, thus increasing the "alertness" of the immune system against cancer cells and improving the defense reaction in such a way that the tumor is fought by the body itself.

Some malign diseases such as advanced renal cell carcinoma seem to be relatively sensitive to immunotherapeutic intervention, however systemic therapy with cytokines such as IL-2 and IFN-alpha is associated with sometimes harsh side effects. Hence, other immunotherapeutic protocols have been developed.

Most clinical studies currently rely on removal of the tumor, subsequent ex-vivo transfection of the tumor cells with a therapeutic gene, radiation of the tumor cell population and subsequent re-implantation of the modified tumor cells. By such tumor vaccination, the anti-tumor response can be increased in differing amounts, depending on the transfected therapeutic gene.

Based on this approach and results from studies in experimental animals, a number of clinical studies of phase I and II were approved (Finke et al., 1997; Wittig et al., 2001).

Preliminary results from these studies, however, indicated that apart from good tolerability of the therapy, partial or complete remissions were observed only in few cases.

Gene transfer of CD40L/CD154 was able to induce eradication of the tumor and immunity in a colon carcinoma mouse model (Sun et al., 2000).

The applicants/assignees of the present application were able to show that transfer of expression plasmids for human interleukin 7 (IL-7) into tumor cells leads to increased sensitivity against effector cells of the immune system, especially in autologous transfer (Finke et al., 1997, Cancer Gene Ther. 4: 260-268). Similarly, the inventors were able to demonstrate that after transfection of two therapeutic genes (IL-7, GM-CSF) into autologous tumor cells, a clinically significant response could be observed in 50% of the patients (WO 02/060476).

It is known from the teaching of U.S. Pat. No. 5,681,562 to inject cells that had been transfected with DNA or RNA encoding cytokines into patients suffering from certain cancers. The immune system of the patient is meant to be stimulated against tumor antigens. In the patent disclosure experiments are described in which murine fibroblasts are transfected by retroviral vectors coding for IL-2. An in-vivo experiment is also described, in which the efficacy of the treatment was tested in a murine colon carcinoma model. Mice that were injected with transfected fibroblasts subcutaneously, developed a significantly slower growth of tumor in comparison to control groups. In-vitro experiments with human transfected fibroblasts showed a significantly increased expression level of IL-2. Apart from the lack of clinical data beyond the mouse model, the viral vectors employed as expression vectors in these experiments are to be regarded as not advantageous. The instability of the attenuated vaccine strain does not allow exclusion of its reversion to a virulent strain, and the viral components can be immunogenic themselves, which results in a their efficacy being decreased by the immune system of the patient. These disadvantages, outlined here only as part of the disadvantages of the viral system, significantly compromise the use of the system as a vector in gene therapy.

Several publications show that the best therapeutic results are attained by combining cytokine genes with the growth factor GM-CSF (Paillard, 1998, Hum. Gene Ther. 9: 2457-2458; Schadendorf et al., 1995, J. Mol. Med. 73: 473-477). The importance of GM-CSF in tumor antigen vaccinations was also shown in the enhancement of the clinical and immunological anti tumor response to peptide vaccination (Jäger et al., 1996). It appears that the activation of antigen-presenting dendritic cells and the stimulation of an effector cell population has a pivotal role in this context.

So far, however, it is unclear what cytokine genes trigger the most effective anti-tumor response in combination with an immunogenic preparation and GM-CSF.

In experiments with mice, it was shown that vaccination with expression constructs encoding IL-7 results in an anti-tumor effect (Miller et al., 1993, Blood 18: 3686-3694; Murphy et al., 1993, J. Clin. Invest. 92: 1918-1924). It is also known that incubation of cytotoxic lymphocytes (CTL) with IL-7 or IL-7 transfected cells leads to tumor regression in mice (Jicha et al., 1991; Hock et al., 1993), and the transfection with IL-7 and B7.1/CD80 leads to infiltration of $CD28^+$ $CD25^+$ T-cells and immunity (Cayeux et al., 1995).

So far, no therapeutic success has been attained, not even in a mouse model.

Furthermore, in experiments relating to the stimulation of immune responses by gene therapy with plasmid DNA or oligonucleotide sequences, it was observed that certain nucleic acid sequences that comprise CpG motifs (CpG=unmethylated cytosine-guanosine dinucleotide) can have an enormous immune stimulatory effect (Schmidt-Wolf et al., 1989, J. Immunol. Methods 125: 185-189). Immune stimulatory sequences (ISS) have been employed very early as adjuvants in DNA based immunization protocols against infectious pathogens for this reason (Sato et al., 1996, Science 273: 352-354). In experiments on mice, it was demonstrated that injection of CpG-rich DNA sequences leads to a strong activation of B-cells and stimulates the expression of certain cytokines, e.g. IL-6 and GM-CSF. It was also shown in a mouse model that immunization with CpG oligodeoxyribonucleosides (ODN) together with a fusion protein three days prior to tumor inoculation could prevent tumor growth in the mouse (Liu et al., 1998). The teaching of use and synthesis of immune stimulatory CpG-containing ISS is explained in detail in WO 98/18810.

From WO 00/04918 it is known to transfect tumor cells with genes encoding, for example, interferon gamma and GM-CSF. As expression vectors, plasmids are used. This application discloses a concept to treat tumor disease by immune therapy. Relevant in-vivo or in-vitro data or clinical results proving the efficacy of the claimed vaccine are not shown. It should be added that these plasmid-based vectors are not useful without restriction for their employment in human gene therapy, since they comprise genetically functional units that are necessary for their replication, apart from the therapeutic sequences. They also comprise antibiotic resistance genes needed for their selection. The result is a continuous expression of therapeutically not desirable mammalian or bacterial proteins.

Despite research over many years and promising approaches it has not been possible to develop an efficacious therapy on the basis of immune functions against tumor diseases by applying immunogenic substances.

OBJECT OR OBJECTS

It is the objective of the present application to provide a vaccine as a pharmaceutical composition for the treatment of diseases that have a relation to cytokines, for example cancer diseases, that is specific and efficiently useful and specifically leads to an induction of tumor specific immune responses. Furthermore, a method to make such vaccine shall also be provided.

SUMMARY

That objective is attained in at least one possible embodiment disclosed herein.

In the context of the application, the following meanings shall be employed:
allogeneic originating from a genetically different individual of the same species, in contrast to "autologous" (cells from the same body)
APC antigen presenting cells
B7.1/CD80 cluster of differentiation 80
CD40L/CD154 cluster of differentiation 40 ligand
DC dendritic cells
dSLIM double Stem-Loop Immunomodulating Oligodeoxyribonucleosides
GM-CSF granulocyte macrophage-colony-stimulating factor
IL-7 interleukin-7
ISS immune stimulatory nucleic acid sequence
MIDGE Minimalistic Immunologically Defined Gene Expression Vector (MIDGE® is a registered trademark of Mologen AG)
ODN oligodeoxyribonucleoside
TAA tumor associated antigens In the following, a number of general terms shall be understood as follows:

Transfected cells in the meaning of the application are human allogeneic tumor cells that were treated ex-vivo with expression vectors encoding according to the invention, and thus express the encoded cytokine and co-stimulatory factor sequences as a consequence of this treatment and can be employed as an immune therapeutic with tumor diseases.

In the context of the present application, the term "co-stimulatory factor" and/or cytokine represents naturally occurring co-stimulatory factors and/or cytokines, as well as all modifications, mutants and derivatives of co-stimulatory factors and/or cytokines, co-stimulatory factors and/or cytokines that have been made by recombinant techniques that contain amino acid modifications as inversions, deletions, insertions, attachments and the like, as long as at least some of the essential functions of the wild type co-stimulatory factors and/or cytokines is retained. Such co-stimulatory factors and/or cytokines can contain unusual amino acids and/or modifications such as alkylation, oxidation, thiol modification, denaturation and oligomerization and the like. In the context of the present application co-stimulatory factors and/or cytokines can be proteins, peptides and/or fusion peptides that contain co-stimulatory factors and/or cytokines in total or partially, in conjunction with other proteins, peptides or parts thereof. In another embodiment of the present application, the co-stimulatory factors and/or cytokines are truncated forms of the naturally occurring co-stimulatory factors and/or cytokines.

All co-stimulatory factors mentioned above that are suitable to modulate the reaction of the immune system are immunogenic substances as defined in the context of the present application. A vaccine according to the present invention therefore is an immunogenic composition, since it contains a combination of immunogenic substances. Tumor cells differ from normal cells, among other qualities, in a different expression of cell surface proteins. Specifically the expression of tumor-associated antigens (TAA) theoretically allows for the recognition and destruction of these cells by the immune system. In many cases, however, the immune system of the patients is suppressed so severely that it does not recognize the mutated cells.

This problem is solved by providing a vaccine for the treatment of patients with defined tumor diseases, whereby this vaccine comprises tumor cells of another patient (allogeneic cells) and these tumor cells have been transfected previously ex-vivo with expression constructs encoding interleukin-7 (IL-7), granulocyte macrophage colony stimulating factor GM-CSF and the co-stimulatory factors CD49L/CD154 and B7.1/CD80. In another embodiment a corresponding vaccine is obtained, whereby the tumor cells are transfected previously with expression constructs encoding interleukin-7 (IL-7), granulocyte macrophage colony stimulating factor GM-CSF and the co-stimulatory factor CD49L/CD154.

The tumor cells that are employed can be derived from a patient with a similar clinical picture as the patient who is to be treated, or from a patient who has a different clinical picture compared to the patient who is to be treated.

The combination of the components (immunogenic compounds) of the vaccine shall guarantee that all three steps of the signal cascade, which are fundamentally required for the induction of a specific immune response, are generated. The three steps comprise antigen presentation, co-stimulation and the provision of a suitable local environment.

Expression of GM-CSF and CD40L/CD154 shall ensure that antigen presenting cells (APC) and dendritic cells (DC) are recruited locally and activated. As a consequence, enhanced presentation of TAA is observed.

Expression of B7.1/CD80 results in increased co-stimulatory activity. This in turn increases the antigenicity of the TAA component and the number of T-lymphocytes that are activated against TAA is increased. Expression of IL-7 additionally induces proliferation of tumor specific T-lymphocytes.

The vaccine according to at least one possible embodiment thus induces a high concentration of soluble proliferation stimulating cytokines and co-stimulatory molecules in conjunction with TAA on the surface of the tumor cells, which leads to activation and proliferation of tumor specific T-cells at the site of application. APC and DC are also enticed to migrate to the site of application.

The expression constructs are either present in the form of plasmid; preferred are also minimalistic immunologic defined gene expression constructs. These are linear double stranded covalently closed expression cassettes comprising essentially only a CMV promoter, an intron, the coding gene sequence and a polyadenylation sequence. The expression cassette is closed covalently on both ends of the double strand by a short loop of single stranded nucleoside residues. These covalently closed minimalistic DNA constructs are referred to in the following as MIDGE vectors (MIDGE: Minimalistic Immunologically Defined Gene Expression Vector); see EP 0 941 318 B1. MIDGE constructs show the advantage that by using them, structures can be avoided that are not essential to the therapeutic effect, thereby avoiding the disadvantages of common gene transfer vehicles.

A local environment that is permissive to the induction of a specific immune response is provided by using an adjuvant in form of immune stimulatory nucleic acid sequences (ISS). In order to attain this objective the application provides for the vaccine containing additional immune modulating oligodeoxyribonucleosides as adjuvant. Preferably, the vaccine comprises a immune modulating oligodeoxyribonucleoside that comprises a) a sequence comprising the base sequence $N^1N^2CGN^3N^4$, where $N^1N^2$ is an element chosen from the group comprising GT, GG, GA, AT or AA, $N^3N^4$ is an element chosen from the group comprising CT or TT, and C is deoxycytosine, G is deoxyguanosine, A is deoxyadenosine and T is deoxythymidine,
  b) and a circular strand of deoxyribonucleic acid with a partially complementary anti-parallel base sequence and is of dumbbell-shaped form.

Figure 2A:
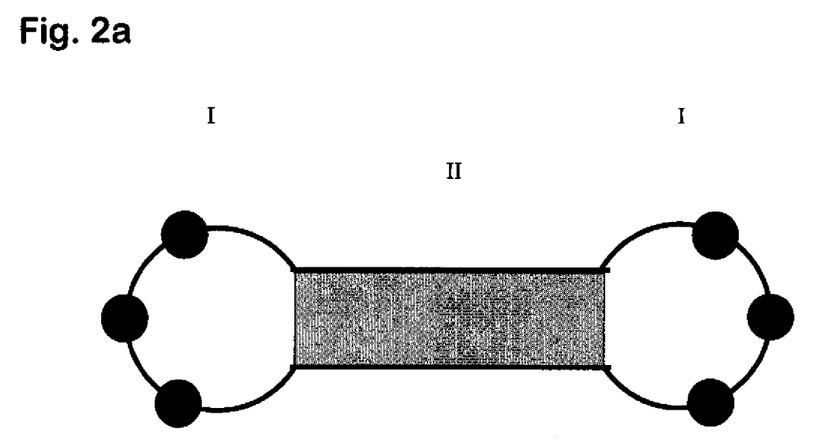
FIGS. 2a and 2b show schematic description of the immune modulators (dSLIM): dumbbell-shaped structure with three CG motifs each in the hairpin loop structure that are schematically depicted; I is loop and II is stem.

The CpG motifs of the ISS (see FIG. 2a) confer an increase of the activity of NK cells and macrophages as well as a strong stimulation of the cellular TH1 type immune response. Thus they serve as immune modulators and allow for and enhance the tumor specific immune response. In a preferred embodiment, covalently closed ISS of 30 base pairs in length are used, as described in WO 01/07055. These constructs are referred to in the following as dSLIM (double Stem-Loop Immunomodulating Oligodeoxyribonucleosides).

Figure 2B:
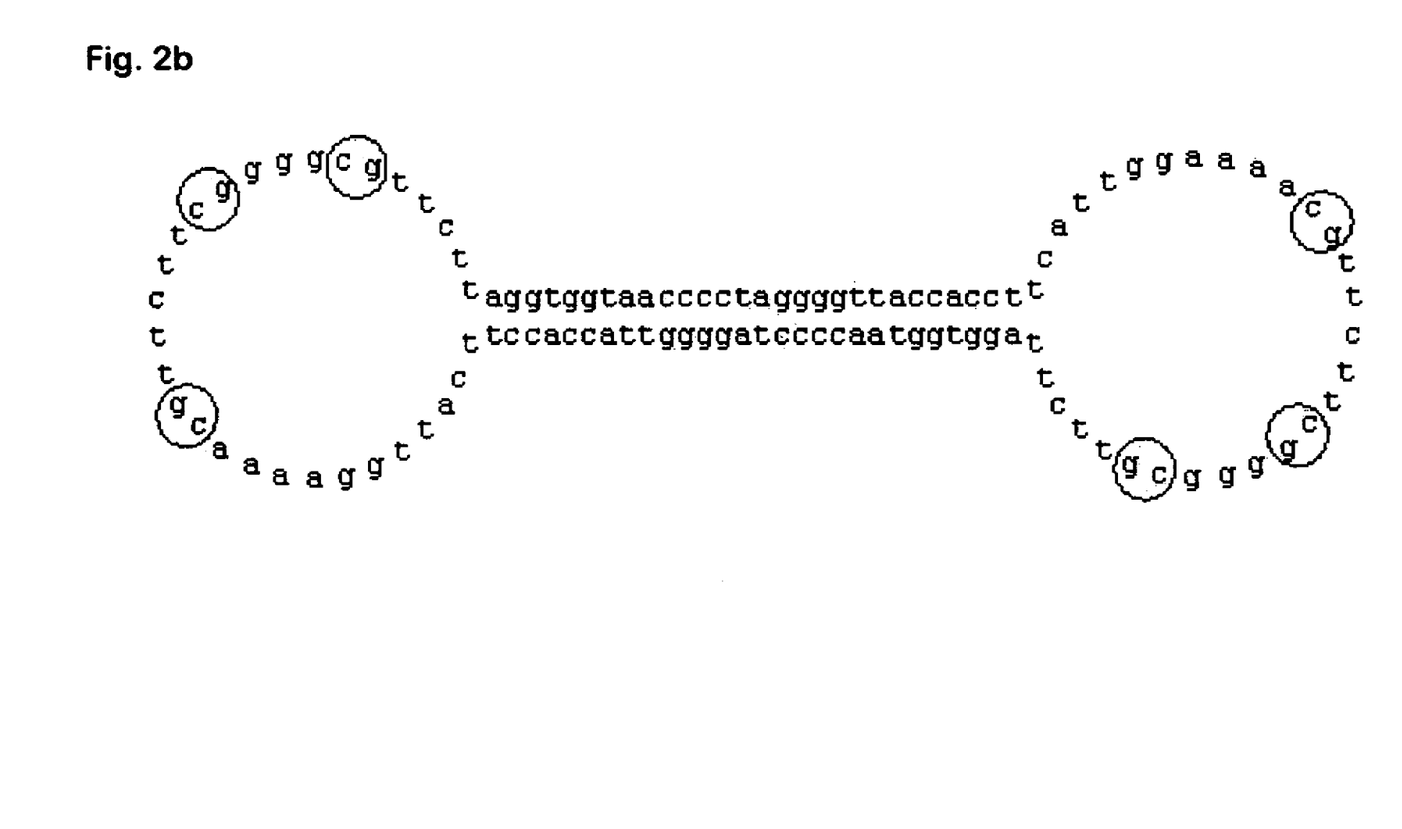

The sequence with the base sequence $N^1N^2CGN^3N^4$ is positioned in the single stranded part of the oligodeoxyribonucleoside and comprises 40 to 200 nucleoside (see FIG. 2b).

Subject of the application is also a method to make a vaccine as described above for the treatment of patients with tumor diseases, whereby tumor cells of a genetically not identical donor of the same species (allogeneic) are transfected ex-vivo with nucleic acid molecules encoding:
  a) Interleukin-7 (IL-7), granulocyte macrophage colony stimulating factor (GM-CSF), CD40L/CD154 and B7.1/CD80, or
  b) Interleukin-7 (IL-7), granulocyte macrophage colony stimulating factor (GM-CSF) and CD40L/CD154
and are subsequently transferred into a applicable pharmaceutical composition. The immune modulating oligodeoxyribonucleosides that were already described above comprise a circular strand of deoxyribonucleic acid with a partially complementary anti-parallel base sequence and are of dumbbell form. They are also part of the method in their quality as an adjuvant.

According to the application, an allogeneic tumor cell is thus provided that contains at least three, preferably four nucleic acid molecules that encode the co-stimulatory factors B7.1/CD80 and CD40L/CD154 and the cytokines interleukin-7 and GM-CSF in conjunction.

Thus, subject of the application are also allogeneic human tumor cells that were transfected accordingly ex-vivo with nucleic acid constructs encoding:
  a) Interleukin-7 (IL-7), granulocyte macrophage colony stimulating factor (GM-CSF), CD40L/CD154 and B7.1/CD80, or
  b) Interleukin-7 (IL-7), granulocyte macrophage colony stimulating factor (GM-CSF) and CD40L/CD154
and comprise the corresponding expression constructs. The tumor cells comprise expression constructs in form of a plasmid or as linear double stranded covalently closed expression cassettes comprising essentially only a CMV promoter, an intron, the coding gene sequence and a polyadenylation sequence closed covalently on both ends of the double strand by a short loop of single stranded nucleoside residues. Preferably, an allogeneic tumor cell of a renal cell carcinoma cell line is employed.

As in the case of the vaccine, the inventive method provides nucleic acid molecules as one or several expression constructs. Thus, a DNA expression construct for multiple gene expression can be provided
  comprising double stranded regions that contain a linear expression cassette that comprises at least a promoter sequence and a coding sequence,
  and where these double stranded regions are linked by DNA single strands or non-coding DNA double strands,
  and the expression cassettes are protected against exonuclease degradation at the ends that are not linked to other expression cassettes by DNA single strands or non-coding DNA double strands.
Such a DNA expression construct for multiple gene expression is already described in PCT/DE03/02478. Therefore, several nucleic acids that are subject of the inventive vaccine can be comprised in one single expression construct.

In an especially preferred embodiment, the nucleic acid molecule is a DNA, specifically a cDNA or genomic DNA. Obviously it can be preferred that the nucleic acid molecule is a RNA molecule. The allogeneic tumor cells are derived from patients with colorectal carcinoma, small cell and non small cell lung carcinoma, prostate carcinoma, mamma carcinoma, ovarian carcinoma and renal cell carcinoma, and malign melanoma. in the course of at least one possible embodiment, a renal cell carcinoma cell line was employed specifically, which is especially suitable for the making of the vaccine according to at least one possible embodiment. A preferred renal cell carcinoma cell line was deposited at the DSMZ (Deutsche Sammlung von Mikroorganismen and Zellkulturen GmbH (German Collection of Microorganisms and Cell Cultures)) as a viable culture under the number DSM ACC 2635. DNA expression constructs are transferred into cells of this line by means of transfection through biological, chemical and/or physical methods that lead to the desired genes being expressed in the cells. An adjuvant, preferably an ISS, most preferred dSLIM (see above) is added to the transfected allogeneic cells. After radioactive irradiation of the transfected allogeneic tumor cells by gamma irradiation, the inventive vaccine is applied to patients who have a tumor disease.

The body that the cells are derived from is not the body that is to be treated with the pharmaceutical composition, in contrast to therapy with autologous cells. The use of allogeneic cells on one hand has the advantage that the cells can be characterized once and reproducibly proliferated. On the other hand, the allogeneic effect is regarded as an additional adjuvant stimulus.

The cells that are to be modified can be derived from a single (different individual) body or can be pooled from several bodies with the same disease picture.

The subject of the application is thus the combination of three or four nucleic acids that can be expressed, and that encode two cytokines and one or two co-stimulatory factors.

ISS, preferably dSLIM, can be used as an additional immune modulator.

Figure 1:
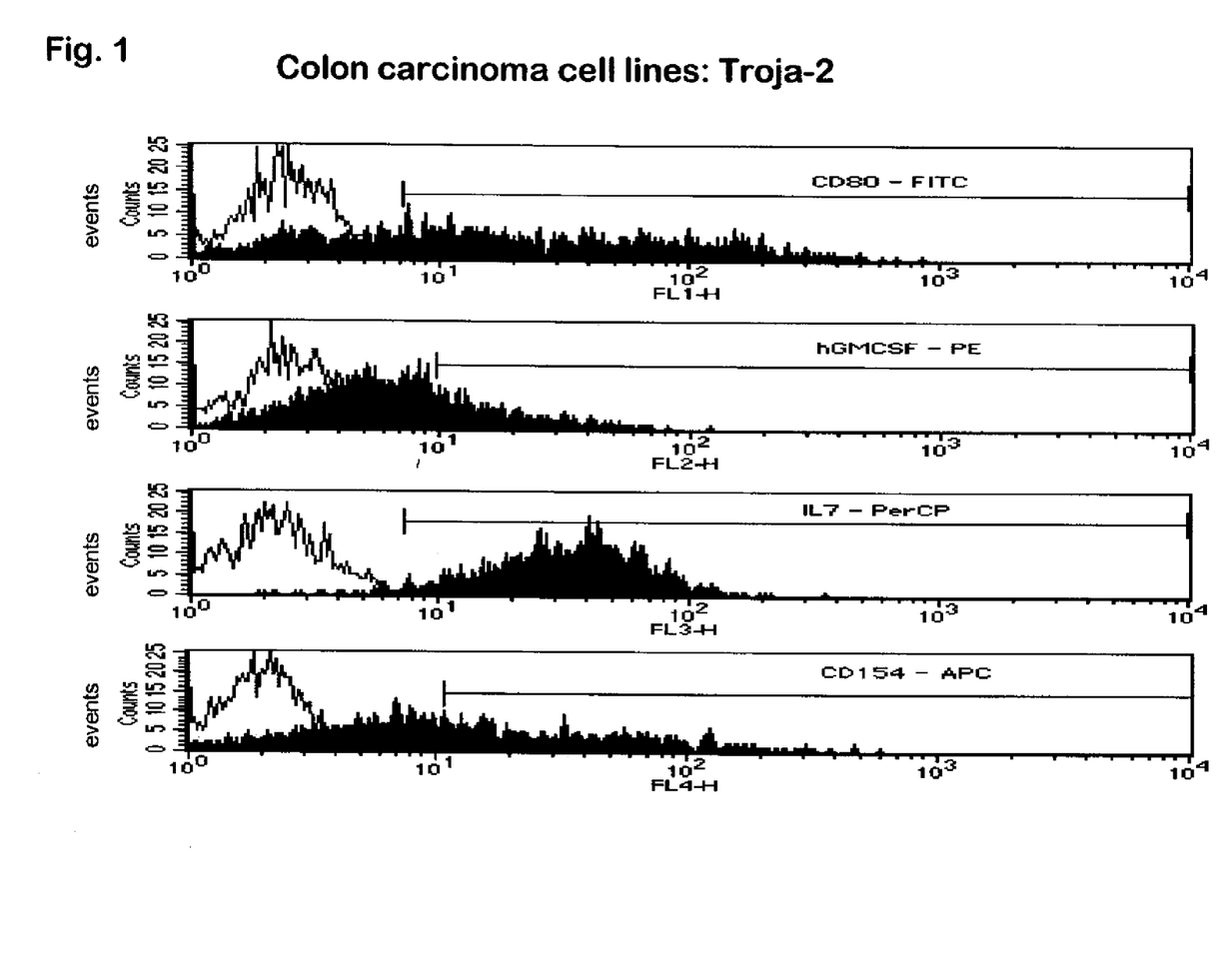
FIG. 1 shows FACS intensities of quadruple transfected human colon carcinoma cells. Transfection was achieved by electroporation with expression vectors encoding CD40L/CD154, GM-CSF, B7.1/CD80 and IL-7.

Cells that were triple or quadruple positive after transfection could be demonstrated in cell culture experiments in primary human cell lines (see FIG. 1). "Triple" or "quadruple" in this context means that a high percentage of the cells were successfully transfected with all of the three or four genes encoding GM-CSF, IL-7, CD40L/CD154 and B7.1/CD80 and that these three or four genes were then expressed by these cells. With the colon carcinoma cell line that was employed in the experiments, 14.4% of all cells could be determined to be quadruple positive by FACS (fluorescence activated cell sorting) analysis. Furthermore, it could be determined that independent of the gene, 20.3% of all cells were successfully transfected with one gene, 19.9% of cells were successfully transfected with three different genes. It was determined that the percentage of successfully transfected colon carcinoma cells after fourfold transfection with expression constructs encoding CD40L/CD154, GM-CSF, B7.1/CD80 and IL-7 was 14.4% of cells. 14.4% of cells thus were transfected with four different genes and capable of expressing those successfully. In total, 69.4% of all cells were transfected with at least one or more of the genes.

It is of advantage to transfect with several genes, since by this way, the expressed cytokines and co-stimulatory factors are expressed in close spatial proximity in the effector organs of the immune system. This spatial proximity is important, since co-stimulatory factors only enhance the vaccination effectively in the context of antigens.

For transfection, essentially known biological, chemical and/or physical methods can be employed, for example transfection by ballistic transfer (EP 0 686 697), polykation transfection, calcium phosphate precipitation, microinjection, protoplast fusion, liposome fusion, viral transfection systems, lipofection and/or electroporation. In a preferred embodiment, transfection is achieved by electroporation.

Further advantageous methods are biological transfection therapy that may lower the rate of recidivism.

Further advantageous embodiments can be derived from the dependent claims and the description. At least one possible embodiment, including the surprising effect of the therapeutic according to the invention as a vaccine for carcinoma therapy, as well as a method are described in more detail in the figures and examples as follows.

The above-discussed embodiments of the present invention will be described further hereinbelow. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

methods such as receptor-mediated gene transfer. Here, in one example DNA expression constructs encoding at least one, preferably two co-stimulatory factors and two cytokines are covalently linked to an oligopeptide, which preferably is the nuclear localization signal (NLS) of the simian virus SV-40.

It is possible to further increase transfection efficacy by using other peptides, which may be made synthetically. This method is especially suitable for cell specific in-vivo gene transfer after intravenous application.

The vaccine in accordance to at least one possible embodiment and made from allogeneic tumor cells according to the inventive method shows surprising effects. Deficits of the immune system of tumor patients can be corrected as well as the intrinsic immune response to tumor specific antigens can be enhanced, both at the same time and in an advantageous fashion.

Furthermore, the vaccine can be employed as an adjuvant therapy for the enhancement and reconstitution of the immune response against residual tumor cells or to deplete the residual tumor mass in patients whose tumor was removed. Hence, a perspective is opened to patients with surgically removed primary tumor without visible metastasis, who could profit from an additional tumor-specific

DESCRIPTION OF EMBODIMENT OR EMBODIMENTS

In order to demonstrate the gene products, antibodies were employed that were linked to four discriminable fluorescence dyes. In FIG. 1, these are termed:
CD80-FITC
hGMCSF-PE
IL7-PerCP
CD154-APC Fluorescence Activated Cell Sorting (FACS) detects these colors in four different channels, termed FL1-H, FL2-H, FL3-H and FL4-H on the x-coordinate. The exponents on the x-axis are giving relative fluorescence intensity. The y-axis shows counts representing approximately the number of detected cells. Analysis is performed by the process of "gating" whereby only cells are counted that fit through a certain gate of energy.

In the following table 1 the percentage of successfully transfected allogeneic renal cell carcinoma cells after triple transfection with expression constructs encoding CD40L/CD154, GM-CSF and IL-7 or quadruple transfection with expression constructs encoding CD40L/CD154, GM-CSF, B7.1/CD80 and IL-7 is given.

TABLE 1

| encoded gene | triple transfection with expression constructs encoding CD40L/CD154, GM-CSF and IL-7 percentage of transfected cells (1 measurement) | quadruple transfection with expression constructs encoding CD40L/CD154, GM-CSF, B7.1/CD80 and IL-7 percentage of transfected cells (2 measurements) |
|---|---|---|
| B7.1/CD80 | — | 66.3-87.6% |
| CD40L/CD154 | 60.8% | 21.6-29.5% |
| IL-7 | 21.7 ng in $1 \times 10^6$ cells | 14.9-38.2 ng in $1 \times 10^6$ cells |
| GM-CSF | 698.9 ng in $1 \times 10^6$ cells | 370.6-1,567.2 ng in $1 \times 10^6$ cells |

Transfection of the co-stimulatory factors B7.1/CD80 and CD40L/CD154 was determined by staining the cells with fluorescently marked antibodies; the degree of transfection with cytokines IL-7 and GM-CSF was determined by measuring the concentration of the cytokines in the medium of cell culture.

The vaccine according to at least one possible embodiment, comprising allogeneic cells transfected ex-vivo, was injected into patients with metastasizing solid tumors at intervals of 7 to 10 days in form of injection cycles comprising two injections each. Cells had been transfected previously by expression vectors encoding IL-7, GM-CSF, CD40/CD154 and/or B7.1/CD80 and had been mixed with immune stimulatory sequences (ISS) subsequently. The first two injections were given on day 1 into the typical sites of vaccination in the skin (intradermally) laterally on the left and right upper arm, on day 7 (to 10) into the typical sites of vaccination in the skin (intradermally) on the upper portion of the left and right upper thigh, on day 14 (to 20) under the skin (subcutaneously) about 30 mm left and right of the navel and on day 21 (to 30) again into the upper arm, but subcutaneously.

All patients were in an advanced state of the disease at the beginning of the treatment. In order to assess the clinical success, the following terms shall be used in accordance to the World Health Organization (1979): a partial response (PR) is a reduction of ascertainable tumor foci by more than 50% over the last four weeks and a suppression of new tumor foci. Stable disease (SD) is the continuation of the state. A mixed response (MR) is a mixed reaction, for instance the progression of metastasizing and a reduction of metastasis in another place. A complete response (CR) is the complete remission of tumor foci.

In the following, at least one possible embodiment shall be explained in more detail by examples, without limiting the application to these examples.

Vaccination

The male patient, suffering from small cell lung carcinoma, received four sequential vaccinations at an interval of seven days with the vaccine according to at least one possible embodiment. The allogeneic renal cell carcinoma cell line had been treated as described above. A control of expression was performed 24 h after transfection. Control of expression of the co-stimulatory factors B7.1/CD80 and CD40L/CD154 was performed by staining the cells with fluorescently labeled antibodies and subsequent analysis by flow cytometry. Determination of the expression of cytokines IL-7 and GM-CSF was performed by measuring the respective concentrations by means of ELISA.

Successfully transfected means: living, positive cells. The data of transfection are given in table 1. The percentage of cells that were successfully transfected with B7.1/CD80 ranged between 66.3 and 87.6%. The percentage of cells that were successfully transfected with CD40L/CD154 ranged between 21.6 and 29.5%. The concentration of the cytokine IL-7 ranged between 14.9 and 38.2 ng per $1 \times 10^6$ cells. The concentration of GM-CSF ranged between 370.6 and 1,567.2 ng per $1 \times 10^6$ cells.

In the case of transfection for triple vaccination with expression constructs encoding CD40L/CD154, GM-CSF and IL-7, the percentage of cells successfully transfected with CD40L/CD154 was 60.8%. The concentration of the cytokine IL-7 was 21.7 ng per $1 \times 10^6$ cells. The concentration of GM-CSF was 698.9 ng per $1 \times 10^6$ cells.

Treatment of Metastasizing Tumor Diseases

Selection of patients: patients with colorectal carcinoma, small cell and non-small cell lung carcinoma, prostate carcinoma, mamma carcinoma, ovarian carcinoma and renal cell carcinoma, as well as malign melanoma, aged 18 to 70 years and a Karnofsky index of 70-100 were eligible for inclusion. Criteria for refusal were: a previous treatment with cytokines or chemotherapy less than 28 prior, creatine values of above 265 micromole/l, bilirubin values of above 51 micromole/l, non-compensated cardiac insufficiency, ventricular dysrhythmia, severe psychiatric disorder, active hepatitis A, B or C, HIV infection.

Treatment: apart from anamnesis, the following parameters were determined prior to treatment: physical examination, hematology (hemoglobin, hematocrit, leukocytes and platelet count), and chemical analysis of blood and urine analysis. Blood was taken to determine immune status. DHT (delayed type hypersensitivity) skin tests were performed with Muititest Merieux assay (Leimen, Germany). X-ray scans and computer tomography of the upper body and abdomen were performed. Patients received four subcutaneous injections with at least $8 \times 10^6$-$1.4 \times 10^7$ cells of previously ex-vivo treated tumor cells. Comprehensive immunological examination, hematological assays and cursory clinical examination (physical examination, ultrasound examination and examination of the lower body, where appropriate) were repeated on days 14, 28 and 56. A complete clinical and immunological examination comparable to the examination performed prior to registration was performed on day 84.

Minimalistic Immunologically Defined Gene Expression Constructs (MIDGE)

Covalently closed minimalistic DNA expression vectors were employed to transfect tumor cells. The expression vectors were used to express human interleukin-7 (IL-7), the human granulocyte macrophage colony-stimulating factor (GM-CSF) and the co-stimulatory factors B7.1/CD80 and CD40L/CD154. MIDGE vectors were synthesized according to SOP procedures in a laboratory conforming to class B with subsequent quality control.

The coding sequences for IL-7 (NCBI Acc. Nr.: J04156), GM-CSF (NCBI Acc.Nr.:M11220), B7.1/CD80 (NCBI Acc.Nr.: AF177937) and CD40L/CD154 (NCBI Acc.Nr.: S49008, taken from the data base (www.ncbi.nlm.nih.gov) of the National Center for Biotechnology Information) were inserted into pMOK plasmids and served as starting material for the synthesis of MIDGE vectors. The plasmid pMOK comprises the strong early immediate promoter from CMV virus, an intron and the polyadenylation sequence of the SV-40 virus (MOLOGEN, Berlin).

The plasmid pMOK encoding IL-7 was digested to completion with the restriction enzyme Eco31I at 37° C. over night. Restriction digestion generated two DNA fragments. One comprised the kanamycin resistance gene and other sequences necessary for the propagation of the plasmid in bacteria. The other fragment comprised the sequences that are part of the MIDGE vector: enhanced CMV-Promoter, chimeric intron, the gene sequence of IL-7 and the polyadenylation sequence from SV-40. 5'-phosphorylated hairpin oligodeoxynucleosides (TIB-MolBiol, Berlin, ODN 1=Seq.ID 5 from WO 03/031469 A2 (Mologen et al.) without modified base X) and ODN2=Seq.ID 6 from WO 03/031469 A2 (Mologen et al.)) were ligated to the MIDGE-forming fragment at 37° C. over night in the presence of T4 DNA ligase and the restriction enzyme Eco31I. In this context, reference is made to the depiction contained in WO 03/031469 A2 (Mologen et al.) and the sequences of oligodeoxynucleosides contained therein. The reaction was stopped by heating to 70° C. The resulting mix of nucleic acids was treated with the enzyme T7 DNA polymerase. MIDGE DNA was purified by anion exchange chromatography and precipitated by isopropanol (see EP 0 941 318 B1).

Synthesis of vectors encoding GM-CSF, B7.1/CD80 and CD40L/CD154 was performed analogously.

Synthesis of MIDGE Linked to NLS

Concerning the synthesis of NLS-MIDGE, reference is made to the description contained in WO 03/031469 A2 (Mologen et al.) and the sequences of oligodeoxynucleosides (ODN) contained therein. The NLS peptide (Seq.ID 4 from WO 03/031469 A2 (Mologen et al.)) is first coupled to the ODN. An ODN 1 linked in its hairpin loop to an amino-modified deoxy-uracil (XT) and an unmodified ODN 2 as described in WO 03/031469 A2 (Mologen et al.) was employed for this reaction:

First the amino-modified oligonucleotide ODN 1 (0.1 mM) was activated by sulfo-KMUS (5 mM) in PBS at room temperature. After 120 min., the reaction was stopped by adding 50 mM tris-(hydroxymethyl)-aminomethane and the activated ODN 1 was obtained after ethanol precipitation (300 mM NaOAc pH 5.2, 5.5 mM $MgCl_2$, 70% ethanol), centrifugation and single washing with 70% ethanol. The ODN 1 (0.1 mM) thus obtained was dissolved in PBS and allowed to react with the NLS peptide (0.2 mM) for one hour at room temperature. The reaction was controlled by gel electrophoresis (3%) and ethidium staining. The NLS-coupled ODN 1 was purified by HPLC and used for synthesis of MIDGE-NLS constructs together with ODN 2 as described above.

Double Stranded Immune-modulatory Oligodeoxynucleosides (d-SLIM)

Double stranded immune-modulatory oligodeoxynucleosides are molecules that comprise CG sequences. To obtain them, linear oligodeoxynucleosides (ODN) are closed covalently by means of a nucleotide loop in order to protect them from degradation by exonucleases. Thus, dumbbell-shaped molecules termed dSLIM, "double stem-loop immunomodulator" are obtained (see FIG. 2). The immune-modulating activity is based on an unspecific activation of the immune system by non-methylated CG sequences that bind to Toll-like receptors. Each loop of the dSLIM contains three non-methylated CG motifs.

Double stranded immune modulators dSLIM of the ISS30 type were synthesized according to a SOP and with subsequent quality control in a class B laboratory. For this, single-stranded hairpin-shaped 5'-phosphorylated oligodeoxyribonucleosides (ODN) were ligated with T4 DNA ligase. After digestion of starting materials with T7 DNA polymerase and chromatographic purification, the ODN were concentrated by ethanol/sodium magnesium acetate precipitation and dissolved in PBS. The detailed procedure can be taken from WO 01/07055. FIG. 2b shows a dSLIM molecule.

Characterization of the Allogeneic Tumor Cell Line

The cell line employed is derived from a primary renal cell carcinoma of a female patient. A cell line was prepared from these primary cells and deposited as a viable culture at the (DSMZ) (Deutsche Sammlung von Mikroorganismen and Zellkulturen GmbH (German Collection of Microorganisms and Cell Cultures)) under accession number DSM ACC2635. After a screening procedure, cells were determined to serve as a starting material for the master cell bank from a number of primary cultures. The cell population had to show stable expression of TAA, a constant and good rate of division and preferably homogeneous growth characteristics. Also, the absence of viral or bacterial contaminants had to be assured.

The renal carcinoma cell line was tested negative for HI virus, Hepatitis B and C virus by a certified laboratory. The HLA type was also characterized, as was expression of TAA and the release of cytokines. To this end, different techniques such as ELISA were established to measure (for example): TNF-alpha, IL-6, GM-CSF and IL-7. Furthermore, intracellular FACS assays and real-time PCR assays were established. After transfection, cells were controlled for the expression of surface antigens, signal transduction molecules and reporter genes. The cell line is characterized by the following immunological values for specific surface markers:

| | |
|---|---|
| EpCAM: | positive |
| Her-2/neu: | negative |
| Cytokeratin 7 + 8: | positive |
| HLA-A1: | positive |
| HLA-A2: | positive |
| Fibroblasts: | negative |

Determination of Tumor-specific Antigens:

| | | | |
|---|---|---|---|
| PRAME: | positive | SCP-1: | positive |
| MAGE-4: | negative | Fertilin-beta: | negative |
| MAGE-3: | negative | RAGE-1: | positive |
| MAGE-1: | negative | G250: | positive |

Electroporation

For the ex-vivo gene transfer into the nucleus of tumor cells and control cells, a preferred method was electroporation. The tumor cells were dissociated from the surface of the culture flask by trypsine/EDTA solution and adjusted to a density of $1-1.5 \times 10^7$ cells per 600 µl in medium (without FCS) or PBS. This volume of 600 µl cell suspension was mixed with 5-10 µg expression vector, transferred into chilled electroporation cuvettes (Eurogentec) and electroporated at a voltage of 300V a capacity of 1050 Mikrofarad in an Easyject electroporation device (EquiBio).

Afterwards, cells are transferred into fresh medium (5-20 ml) and incubated in a cell culture incubator (5% $CO_2$, 37° C., saturated humidity) for 24 h. The measurement of surface molecules (CD40L/CD154 and B7.1/CD80) and cytokines (GM-CSF and IL-7) by four-color flow cytometry follows thereafter. Cell number and vitality are controlled as well.

Immediately after gene transfer, the tumor cells are covered with 10 ml warmed cell suspension medium and transferred into 15 ml centrifuge tubes by cautious pipetting. After sedimentation of the cells at 300×G and 4° C. for 5 min, they were resuspended in medium. Again, aliquots were taken for sterility testing, assays for cell reconstitution and vitality, FACS analysis and for determination of the cytokine expression were taken. Transfection efficacy was determined as described (Foa et al., 1994, Nat. Immun. 13: 65-75))

The transfected tumor cell suspension was dried again, re-suspended in 1.5 ml freezing medium (80% FCS, 10% DMSO, 10% suspension medium) and kept in aliquots of 8×10⁶ bis 1.4×10⁷ cells in sealed freezer tubes of 2 ml. Tubes were frozen to −80° C. at 1° C. per minute and kept in liquid nitrogen.

Completion of the Inventive Vaccine

After careful thawing of the freezer tubes, the cell count was determined again and aliquots were taken for sterility tests. After careful and repeated washing of the cells, the cell pellet was re-suspended in Dulbecco's Phosphate Buffered Saline (DPBS, Camprex Kat. Nr.: 17-512F). Depending on the lot, 500 microgram of the adjuvant dSLIM was added. The completed vaccine was transferred endotoxin-free reaction vessel. Each 750 microliters were drawn into a syringe through a needle.

Prior to application, a five-fold irradiation of the syringes with gamma rays, corresponding to a total dose of 150 Gray, was performed.

Lymphocyte Preparation

Peripheral blood monocytes (PBMC) were prepared from heparine-treated peripheral blood by Lymphoprep (GIBCO, Karlsruhe) and density gradient centrifugation. The cells were washed twice with PBS and freeze-dried in liquid nitrogen in the presence of more than 20% FCS for ELISPOT and cytotoxic assays.

Statistical Analysis

Wilcoxons adapted pairwise and nonpairwise test was used to analyze statistical significance. A p-value of <0.05 is regarded as significant.

The Sequence Listing submitted herewith is hereby incorporated by reference and should be considered as part of the disclosure. The sequence listed therein, having Seq. ID 1, is as follows: cctaggggtt accaccttca ttggaaaacg ttcttcgggg cgttct- tagg tggtaacccc taggggttac caccttcatt ggaaaacgtt cttcggggcg ttcttaggtg gtaacc.

One feature or aspect of an embodiment is believed at the time of the filing of this patent application to possibly reside broadly in a vaccine for the treatment of patient who suffer from tumor diseases, containing tumor cells of a genetically not identical (different) donor of the same species (allogeneic), where the tumor cells were transfected previously ex-vivo with nucleic acid molecules encoding interleukin-7 (IL-7), granulocyte-macrophage colony stimulating factor (GM-CSF), CD40L/CD154 and B7.1/CD80.

Another feature or aspect of an embodiment is believed at the time of the filing of this patent application to possibly reside broadly in a vaccine for the treatment of patient who suffer from tumor diseases, containing tumor cells of a genetically not identical (different) donor of the same species (allogeneic), where the tumor cells were transfected previously ex-vivo with nucleic acid molecules encoding interleukin-7 (IL-7), granulocyte-macrophage colony stimulating factor (GM-CSF) and CD40L/CD154.

Yet another feature or aspect of an embodiment is believed at the time of the filing of this patent application to possibly reside broadly in a vaccine where the encoding nucleic acid constructs are present in one or more expression constructs.

Still another feature or aspect of an embodiment is believed at the time of the filing of this patent application to possibly reside broadly in a vaccine, where the expression construct is a) a plasmid or b) a linear double stranded, covalently closed expression cassette consisting solely of a CMV promoter, an intron, the encoding gene sequence and a polyadenylation sequence being closed on both ends of the double strand by a short loop of single stranded nucleoside residues.

A further feature or aspect of an embodiment is believed at the time of the filing of this patent application to possibly reside broadly in a vaccine, where said vaccine comprises additional immune modulating oligodeoxynucleosides as an adjuvant.

Another feature or aspect of an embodiment is believed at the time of the filing of this patent application to possibly reside broadly in a vaccine, where the immune modulating oligodeoxynucleotide a) comprises a sequence of the base sequence $N^1N^2CGN^3N^4$, where $N^1N^2$ is an element selected from the group comprising GT, GG, GA, AT or AA, $N^3N^4$ is an element selected from the group comprising CT or TT, and C is desoxycytosine, G is desoxyguanosine, A is desoxyadenosine and T is desoxythymidine, b) and comprises a circular strand deoxyribonucleic acid with a partially complementary antiparallel base sequence and is of dumbbell shaped form.

Yet another feature or aspect of an embodiment is believed at the time of the filing of this patent application to possibly reside broadly in a vaccine, where the sequence with the base sequence $N^1N^2CGN^3N^4$ is positioned in the single stranded region of the oligodeoxyribonucleoside and comprises 40 to 200 nucleoside.

Still another feature or aspect of an embodiment is believed at the time of the filing of this patent application to possibly reside broadly in a vaccine, where said vaccine comprises a pharmaceutically acceptable carrier.

A further feature or aspect of an embodiment is believed at the time of the filing of this patent application to possibly reside broadly in a vaccine, where the allogeneic tumor cells are selected from colorectal carcinoma, small cell or non-small cell lung carcinoma, prostate carcinoma, mamma carcinoma, ovarian carcinoma, renal cell carcinoma and malign melanoma.

Another feature or aspect of an embodiment is believed at the time of the filing of this patent application to possibly reside broadly in a vaccine, where the tumor cells are derived from the renal cell carcinoma deposited under accession number DSM ACC 2635 at the DSMZ.

Yet another feature or aspect of an embodiment is believed at the time of the filing of this patent application to possibly reside broadly in a method to make a vaccine for the treatment of patient who suffer from tumor diseases, where tumor cells of a genetically not identical (different) donor of the same species (allogeneic) are transfected ex-vivo with nucleic acid molecules encoding a) interleukin-7 (IL-7), granulocyte-macrophage colony stimulating factor (GM-CSF), CD40L/CD154 and B7.1/CD80, or b) interleukin-7 (IL-7), granulocyte-macrophage colony stimulating factor (GM-CSF), and CD40L/CD154 and subsequently are transferred into a applicable pharmaceutical composition.

Still another feature or aspect of an embodiment is believed at the time of the filing of this patent application to possibly reside broadly in a method, where additionally, immune modulating oligodeoxyribonucleosides are employed as an adjuvant.

A further feature or aspect of an embodiment is believed at the time of the filing of this patent application to possibly reside broadly in a method, where the immune modulating oligodeoxyribonucleoside comprises a circular strand of deoxyribonucleic acid with a partially complementary, anti-parallel base sequence and is of a dumbbell shape.

Another feature or aspect of an embodiment is believed at the time of the filing of this patent application to possibly reside broadly in a method, where the immune modulating oligodeoxyribonucleoside comprises a sequence of the base sequence $N^1N^2CGN^3N^4$, where $N^1N^2$ is an element selected from the group comprising GT, GG, GA, AT or AA, $N^3N^4$ is an element selected from the group comprising CT or TT, and C is desoxycytosine, G is desoxyguanosine, A is desoxyadenosine and T is desoxythymidine.

Yet another feature or aspect of an embodiment is believed at the time of the filing of this patent application to possibly reside broadly in a method, where the sequence with the base sequence $N^1N^2CGN^3N^4$ is positioned in the single stranded region of the oligodeoxyribonucleoside and comprises 40 to 200 nucleoside.

Still another feature or aspect of an embodiment is believed at the time of the filing of this patent application to possibly reside broadly in a method, where the nucleic acid molecules are present in one or several expression constructs.

A further feature or aspect of an embodiment is believed at the time of the filing of this patent application to possibly reside broadly in a method, wherein the transfection method being ballistic transfer, polykation transfection, calcium phosphate precipitation, microinjection, protoplast fusion, liposome fusion, viral transfection systems, lipofection and/or electroporation.

Another feature or aspect of an embodiment is believed at the time of the filing of this patent application to possibly reside broadly in a method, where the allogeneic tumor cells are selected from colorectal carcinoma, small cell or non-small cell lung carcinoma, prostate carcinoma, mamma carcinoma, ovarian carcinoma, renal cell carcinoma and malign melanoma.

Yet another feature or aspect of an embodiment is believed at the time of the filing of this patent application to possibly reside broadly in a method, where the tumor cells are derived from several patients with the same disease picture.

Still another feature or aspect of an embodiment is believed at the time of the filing of this patent application to possibly reside broadly in a method, where the tumor cells of the renal carcinoma cell line deposited under accession number DSM ACC 2635 at the DSMZ are employed.

A further feature or aspect of an embodiment is believed at the time of the filing of this patent application to possibly reside broadly in a human tumor cell transfected ex-vivo with nucleic acid molecules encoding a) interleukin-7 (IL-7), granulocyte-macrophage colony stimulating factor (GM-CSF), CD40L/CD154 and B7.1/CD80, or b) interleukin-7 (IL-7), granulocyte-macrophage colony stimulating factor (GM-CSF), and CD40L/CD154 and comprising the corresponding expression constructs.

Another feature or aspect of an embodiment is believed at the time of the filing of this patent application to possibly reside broadly in a human tumor cell, where the expression construct is a) a plasmid or b) a linear double stranded, covalently closed expression cassette consisting solely of a CMV promoter, an intron, the encoding gene sequence and a polyadenylation sequence being closed on both ends of the double strand by a short loop of single strands nucleoside residues.

Yet another feature or aspect of an embodiment is believed at the time of the filing of this patent application to possibly reside broadly in a human tumor cell, where said tumor cell is an allogeneic tumor cell of a renal cell carcinoma cell line.

Still another feature or aspect of an embodiment is believed at the time of the filing of this patent application to possibly reside broadly in a human tumor cell, where the tumor cells are the renal carcinoma cell line deposited under accession number DSM ACC 2635 at the DSMZ.

A further feature or aspect of an embodiment is believed at the time of the filing of this patent application to possibly reside broadly in a human tumor cell for the use as a vaccine for the treatment of tumor diseases.

Another feature or aspect of an embodiment is believed at the time of the filing of this patent application to possibly reside broadly in a composition comprising tumor cells of a genetically not identical (different) donor of the same species (allogeneic), where the tumor cells comprise ex-vivo-transfected, encoding nucleic acid molecules which encode one of: a) interleukin-7 (IL-7), granulocyte-macrophage colony stimulating factor (GM-CSF), CD40L/CD154 and B7.1/CD80; or b) interleukin-7 (IL-7), granulocyte-macrophage colony stimulating factor (GM-CSF) and CD40L/CD154.

The components disclosed in the various publications, disclosed or incorporated by reference herein, may possibly be used in possible embodiments, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

All of the patents, patent applications or patent publications, which were cited in the International Search Report mailed Dec. 29, 2004, for International Patent Application No. PCT/DE2004/000859, and/or cited elsewhere are hereby incorporated by reference as if set forth in their entirety herein.

The corresponding foreign and international patent publication applications, namely, International Patent Application No. PCT/DE2004/000859 (filed on Apr. 20, 2004, and International Patent Application No: PCT/DE2003/04299 filed on Dec. 30, 2003, each having inventors Tomislav Dobric, Burghardt Wittig, and Manuel Schmidt, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior, art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72 (b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A vaccine for the treatment of patients who suffer from tumor diseases, said vaccine containing transfected tumor cells of a genetically not identical (different) donor of the same species (allogeneic), wherein the tumor cells were transfected ex-vivo with nucleic acid molecules encoding:
   interleukin-7 (IL-7), granulocyte-macrophage colony stimulating factor (GM-CSF), CD40L/CD154 and B7.1/CD80.

2. The vaccine according to claim 1, wherein the encoding nucleic acid molecules are present in one or more expression constructs.

3. The vaccine according to claim 2, wherein the expression construct is one of:
   a) a plasmid; or
   b) a linear double stranded, covalently closed expression cassette comprising essentially solely a CMV promoter, an intron, the encoding gene sequence and a polyadenylation sequence being closed on both ends of the double strand by a short loop of single stranded nucleotide residues.

4. The vaccine according to claim 3, wherein:
   said vaccine comprises additionally an immune modulating oligodeoxyribonucleotide as an adjuvant; and the immune modulating oligodeoxynucleotide:
   a) comprises a sequence of the base sequence $N^1N^2CGN^3N^4$, where $N^1N^2$ is an element selected from the group comprising GT, GG, GA, AT or AA, $N^3N^4$ is an element selected from the group comprising CT or TT, and C is desoxycytosine, G is desoxyguanosine, A is desoxyadenosine and T is desoxythymidine,
   b) and comprises a circular strand deoxyribonucleic acid with a partially complementary antiparallel base sequence and is of a dumbbell shape.

5. The vaccine according to claim 4, wherein the sequence with the base sequence $N^1N^2CGN^3N^4$ is positioned in the single stranded region of the oligodeoxyribonucleotide and comprises 40 to 200 nucleotides; and
   said vaccine comprises a pharmaceutically acceptable carrier.

6. The vaccine according to claim 1, wherein the allogeneic tumor cells are selected from colorectal carcinoma, small cell or non-small cell lung carcinoma, prostate carcinoma, mamma carcinoma, ovarian carcinoma, renal cell carcinoma and malign melanoma.

7. The vaccine according to claim 5, wherein the tumor cells are derived from the renal cell carcinoma cell line deposited under accession number DSM ACC 2635 at the DSMZ.

8. A method of making a vaccine according to claim 1 for the treatment of patients who suffer from tumor diseases, wherein tumor cells of a genetically not identical (different) donor of the same species (allogeneic) are transfected ex-vivo with nucleic acid molecules encoding:
   interleukin-7 (IL-7), granulocyte-macrophage colony stimulating factor (GM-CSF), CD40L/CD154 and B7.1/CD80
   and subsequently are transferred into a an applicable pharmaceutical composition.

9. The method according to claim 8, wherein:
   additionally, an immune modulating oligodeoxyribonucleotide is employed as an adjuvant; and the immune modulating oligodeoxyribonucleotide comprises a circular strand of deoxyribonucleic acid with a partially complementary, antiparallel base sequence and is of a dumbbell shape.

10. The method according to claim 9, wherein: the immune modulating oligodeoxyribonucleotide comprises a sequence of the base sequence $N^1N^2CGN^3N^4$, where $N^1N^2$ is an element selected from the group comprising GT, GG, GA, AT or AA, $N^3N^4$ is an element selected from the group comprising CT or TT, and C is desoxycytosine, G is desoxyguanosine, A is desoxyadenosine and T is desoxythymidine; and
   the sequence with the base sequence $N^1N^2CGN^3N^4$ is positioned in the single stranded region of the oligodeoxyribonucleotide and comprises 40 to 200 nucleotides.

11. The method according to claim 8, wherein at least one of:
   the nucleic acid molecules are present in one or several expression constructs; and
   the allogeneic tumor cells are selected from colorectal carcinoma, small cell or non-small cell lung carcinoma, prostate carcinoma, mamma carcinoma, ovarian carcinoma, renal cell carcinoma and malign melanoma.

12. The method according to claim 8, wherein the transfection method being ballistic transfer, polycation, transfection, calcium phosphate precipitation, microinjection, protoplast fusion, liposome fusion, viral transfection systems, lipofection and/or electroporation.

13. The method according to claim 9, wherein the tumor cells are derived from several patients with the same disease picture.

14. The method according to claim 8, wherein the tumor cells of the renal cell carcinoma cell line deposited under accession number DSM ACC 2635at the DSMZ are employed.

15. A human tumor cell transfected ex-vivo with nucleic acid molecules encoding:
   interleukin-7 (IL-7), granulocyte-macrophage colony stimulating factor (GM-CSF), CD40L/CD154 and B7.1/CD80.

16. The human tumor cell according to claim 15, wherein the expression construct is:
   a) a plasmid; or
   b) a linear double stranded, covalently closed expression cassette comprising essentially solely a CMV promoter, an intran, the encoding gene sequence and a polyadenylation sequence being closed on both ends of the double strand by a short loop of single stranded nucleotide residues.

17. The human tumor cell according to claim 16, wherein said tumor cell is an allogeneic tumor cell of a renal cell carcinoma cell line.

18. The human tumor cell according to claim 17, wherein the tumor cells are from the renal cell carcinoma cell line deposited under accession number DSM ACC 2635 at the DSMZ.

19. A composition comprising tumor cells of a genetically not identical (different) donor of the same species (allogeneic), wherein the tumor cells comprise ex-vivo-transfected, encoding nucleic acid molecules which encode:
- interleukin-7 (IL-7), granulocyte-macrophage colony stimulating factor (GM-CSF), CD40L1CD154 and B7.1/CD80.

20. A human tumor cell for use as a vaccine in the treatment of tumor diseases comprising: tumor cells from the renal cell carcinoma cell line deposited under accession number DSM ACC 2635 at the DSMZ that has been transfected ex-vivo with nucleic acid molecules encoding:
- interleukin-7 (IL-7), granulocyte-macrophage colony stimulating factor (GM-CSF), CD40L/CD154 and B7.1/CD80
- and a corresponding expression construct, wherein the expression construct is a plasmid or a linear double stranded, covalently closed expression cassette comprising essentially solely a CMV promoter, an intron, the encoding gene sequence and a polyadenylation sequence being closed on both ends of the double strand by a short loop of single stranded nucleotide residues.

* * * * *